United States Patent [19]

McDonald

[11] Patent Number: 5,203,789
[45] Date of Patent: Apr. 20, 1993

[54] FOLDABLE PLASTIC OPTICAL LENS WITH REDUCED THICKNESS LIGHT BLOCKING SEGMENTS

[75] Inventor: Henry H. McDonald, 65 N. Madison, Suite 810, Pasadena, Calif. 91101

[73] Assignees: Henry H. McDonald; William W. Haefliger, both of Pasadena, Calif.; a part interest

[21] Appl. No.: 791,002

[22] Filed: Nov. 12, 1991

[51] Int. Cl.⁵ ............................................. A61F 2/16
[52] U.S. Cl. ................................................... 623/6
[58] Field of Search ............................................ 623/6

[56] References Cited

U.S. PATENT DOCUMENTS

| | | | |
|---|---|---|---|
| 4,605,409 | 8/1986 | Kelman | 623/6 |
| 4,786,445 | 11/1988 | Portnoy et al. | 623/6 |
| 4,813,957 | 3/1989 | McDonald | 623/6 |
| 4,834,751 | 5/1989 | Knight et al. | 623/6 |
| 4,842,602 | 6/1989 | Nguyen | 623/6 |
| 4,880,426 | 11/1989 | Ting et al. | 623/6 |
| 4,888,013 | 12/1989 | Ting et al. | 623/6 |
| 4,888,014 | 12/1989 | Nguyen | 623/6 |
| 4,894,062 | 1/1990 | Knight et al. | 623/6 |
| 4,932,970 | 6/1990 | Portney | 623/6 |
| 4,938,767 | 7/1990 | Ting et al. | 623/6 |
| 4,957,505 | 9/1990 | McDonald | 606/107 |
| 4,959,070 | 9/1990 | McDonald | 606/107 |
| 4,978,354 | 12/1990 | Van Gent | 623/6 |
| 5,030,231 | 7/1991 | Portney | 623/6 |
| 5,044,743 | 9/1991 | Ting | 623/6 |

Primary Examiner—Randy C. Shay
Attorney, Agent, or Firm—William W. Haefliger

[57] ABSTRACT

A foldable plastic lens insertable into the eye lens zone from which a natural lens has been removed comprising the plastic lens having a light passing intermediate and bead-like optical portion, and two oppositely extending haptics; the lens also having two opposed peripheral segments characterized as light blocking; and the segments having substantially reduced thickness relative to the thickness or thicknesses of the main extent of the intermediate optical portion.

13 Claims, 4 Drawing Sheets

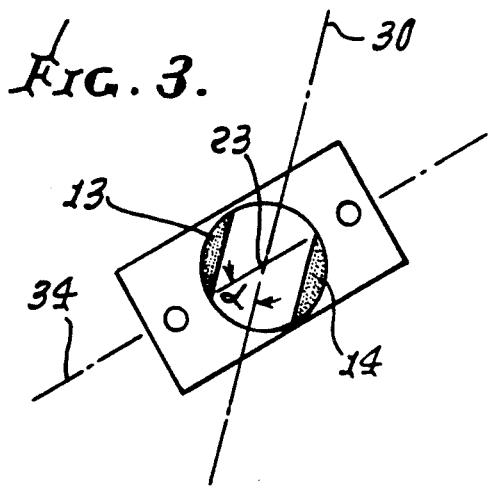
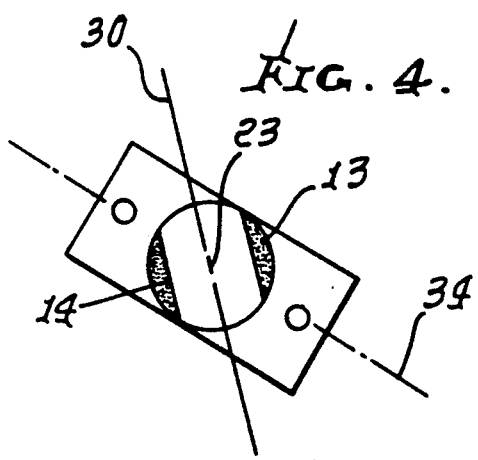
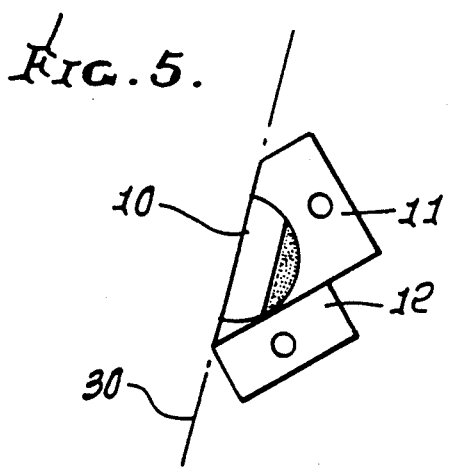
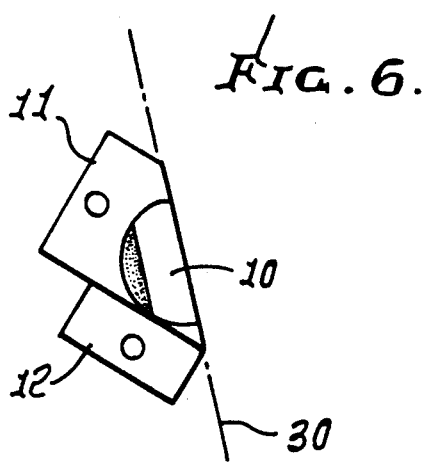
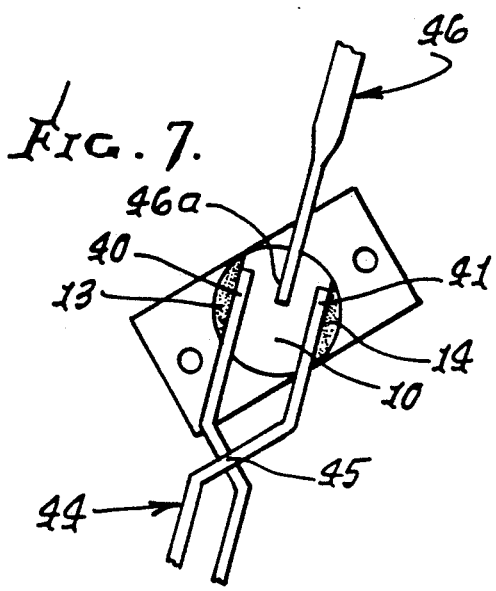
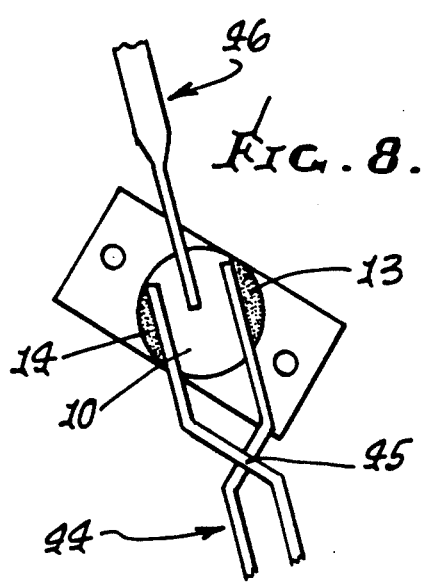

FOLDABLE PLASTIC OPTICAL LENS WITH REDUCED THICKNESS LIGHT BLOCKING SEGMENTS

BACKGROUND OF THE INVENTION

This invention relates generally to method and apparatus for insertion of a folded silicon lens through a narrow width incision in the eye, and into the corneo-scleral limbus of the eye, more particularly it concerns formation and use of a foldable lens having light occluding, de-bulked portions or segments to facilitate such insertion.

Recent efforts to achieve clear vision by use of a lens implant have led to use of hard plastic lens of narrowed width to be passed through an incision or wound (of about 7 mm length) in the eye surface. However, visual distortion can then result, because external light rays can then pass through the pupil extents not covered by the reduced lens implant dimension, as during de-centering of the lens implant in the eye.

There is, accordingly, need for a means to alleviate the problem of such visual distortion, as well as need for improvement in soft lenses that will avoid the distortion problem as well as aid insertion of such lenses.

SUMMARY OF THE INVENTION

It is a major object of the invention to provide a special lens implant which overcomes the above problems, in a very simple manner. The invention contemplates use of a foldable silicone lens having abruptly reduced bulk and thickness, at an opaque edge segment or segments, which may complete the lens fold cross-dimension (typically about 6 mm).

Basically, the foldable malleable silicon lens of the present invention incorporates at least one de-bulked or thinned peripheral segment and preferably two peripheral segments, which enable or facilitate folding, especially folding of haptics connected to the lens, such segments also characterized as occluded or darkened to prevent light ray passage. Such segments are positioned at locations such that the light passing extent of the lens has reduced width (as referred to above) between the segments, but can have normal width (up to 6 mm) along an axis parallel to the segments, the lens being foldable to pass through the narrow width incision in the eye. The reduced thickness segments also form pockets to receive and locate the forceps blades during lens folding, implantation, and unfolding in the eye, for better and more reliable control of these steps, as will be seen.

It is another object of the invention to provide an implantable folded lens that facilitates insertion through an incision in the eye, and which also enables reduction in lens size, through use of occluded lens segments, de-bulked in size. Basically, the lens of the invention is characterized as a) having a light passing intermediate and bead-like optical portion, and two oppositely extending haptics, b) the lens also having two opposed peripheral segments characterized as light blocking, c) said segments having substantially reduced thickness relative to the thickness or thicknesses of the main extent of said intermediate optical portion.

As will be seen the two segments are typically of substantially equal size and shape, and may extend adjacent the intermediate optical portion along a substantially linear border. Further, the lens has an optical axis, and there being a flat plane containing said optical axis which bisects one of the segments and also bisects the other of the segments.

It is another object to provide a lens as referred to wherein the haptics are in the form of flat, foldable and flexible plastic tabs that extend directionally longitudinally oppositely, the segments each elongated in skewed relation to said haptics longitudinal direction. The lens is typically foldable along a fold axis parallel to the two segments, to bring the flexible segments into superposition for insertion through a very small width eye incision, and into the corneo-scleral limbus. The two segments may abruptly taper away from the intermediate optical portion of the lens, and the lens may be gripped by forceps at the superposed reduced thickness segments to enhance grippability of the folded lens, as during its insertion into the eye along with haptics attached to the lens, to ensure gripping of the folded lens during its controlled rotary positioning in the eye, and to enable controlled release and expansion of the folded lens, i.e. prevent "explosive expansion".

The basic method of the invention includes the steps
i) folding the lens to superimpose said segments,
ii) causing the blades to grip the folded lens at or proximate said superposed segments, and
iii) inserting the folded lens into the eye via the incision.

As noted, the method may advantageously include engaging the blades against the reduced thickness segments during progressive folding of the lens, and during progressive unfolding of the lens, in the eye.

These and other objects and advantages of the invention, as well as the details of an illustrative embodiment, will be more fully understood from the following specification and drawings, in which:

DRAWING DESCRIPTION

FIG. 3 is a front view of a lens as in FIG. 1, together with attached solid haptics;

FIG. 4 is a rear view of the FIG. 3 lens and haptics;

FIG. 5 is a front view of the FIG. 3 lens and haptics in folded condition;

FIG. 6 is a rear view of the FIG. 5 folded lens and haptics;

FIG. 7 is a front view showing use of holding and folding forceps during lens folding;

FIG. 8 is a rear view of the FIG. 7 forceps and lens, during folding;

Figure 13:
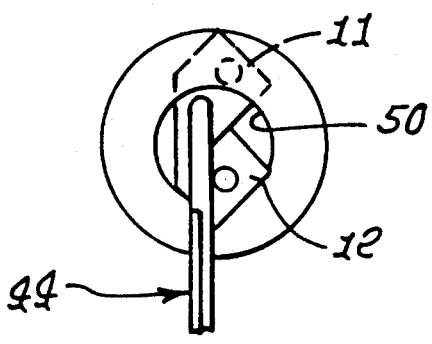
Figure 14:
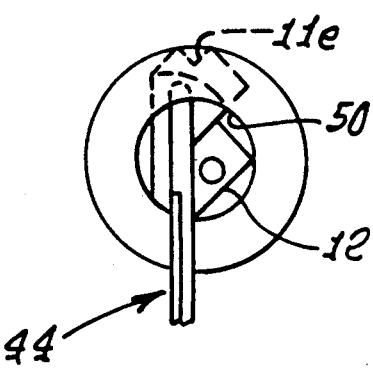
Figure 9A:
Figure 9B:
Figure 9C:
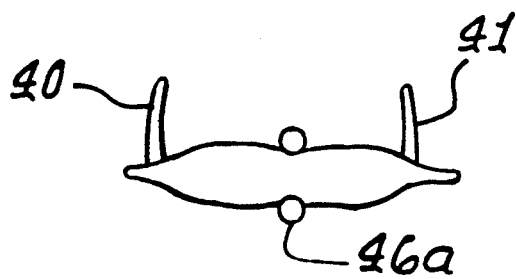
Figure 9D:
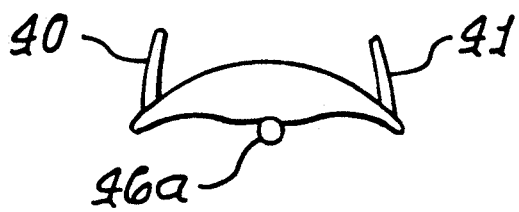
Figure 9E:
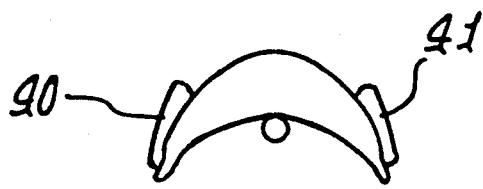
Figure 9:
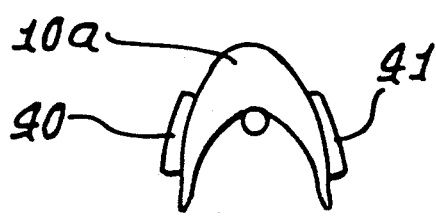
Figure 9G:
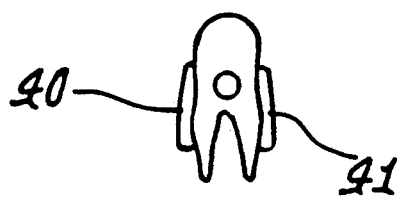
Figure 11:
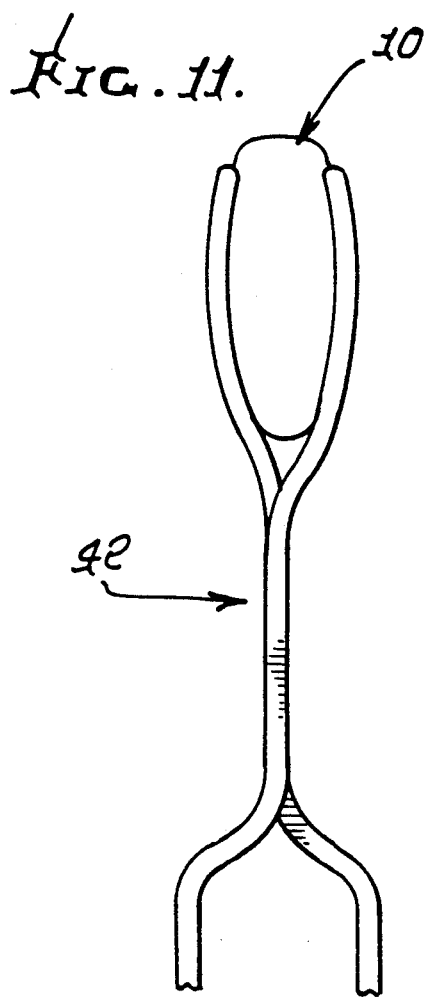
Figure 12:
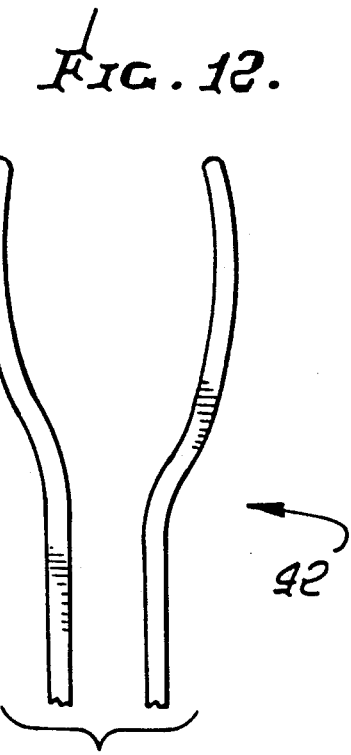
Figure 10:
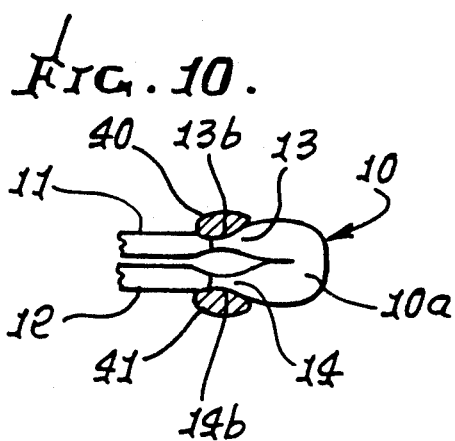

FIGS. 9 (a)–(g) are views showing progressive folding of the lens;

FIG. 10 is an edge view of a folded lens with folding forceps received in pockets formed by light blocking peripheral segments of reduced "de-bulked" thickness;

FIG. 11 is an enlarged view showing forceps blades holding a lens in folded condition;

FIG. 12 shows the FIG. 11 forceps blades in released condition;

FIGS. 13 and 14 show folded lens insertion into the eye; and

Figure 15:
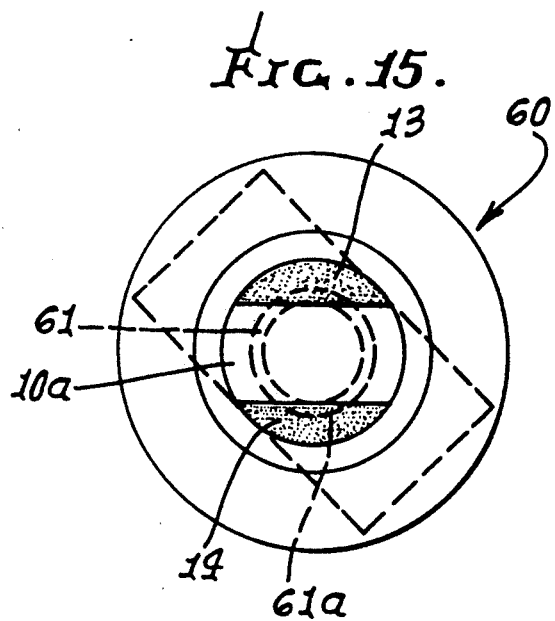

FIG. 15 shows the released lens and light blocking segments in the eye.

DETAILED DESCRIPTION

Figure 1:
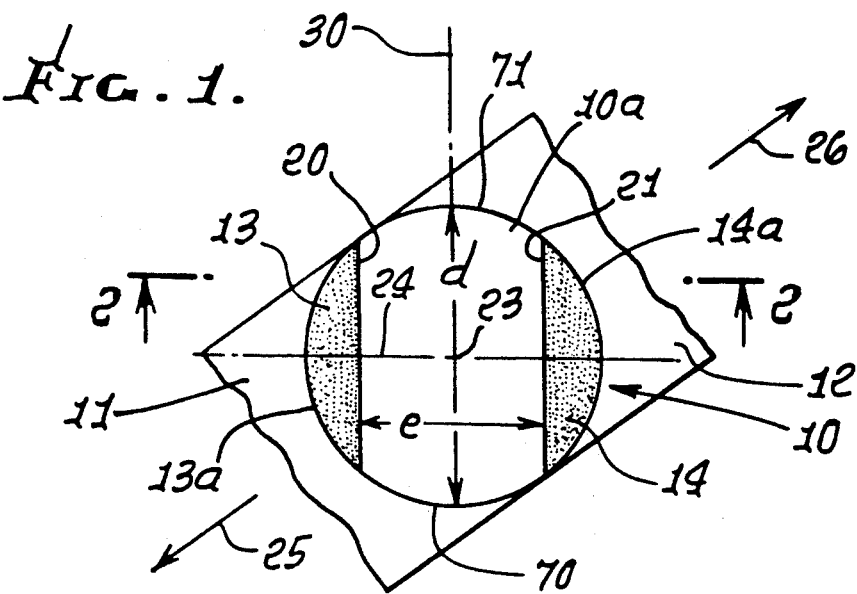
FIG. 1 is a front view of a modified plastic lens incorporating the invention.
Figure 2:
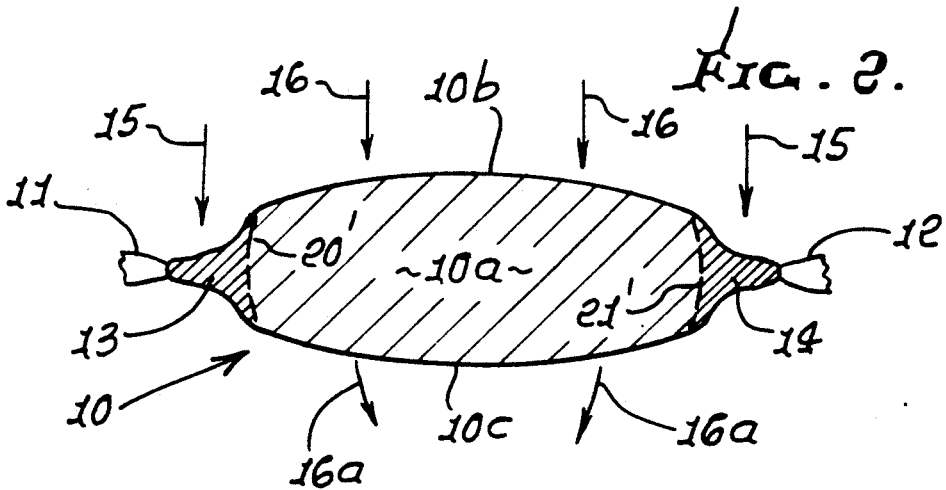
FIG. 2 is an enlarged section taken on lines 2—2 of FIG. 1.

In FIGS. 1 and 2, a plastic, silicon lens 10 is shown, sized for resiliently yieldable folding and insertion into the eye lens zone from which a natural but cataractous lens has been removed. One highly advantageous technique for such insertion is disclosed in U.S. Pat. No. 4,813,957, other techniques being usable. The bead-like lens has a light passing intermediate zone 10a between outwardly convex lens surfaces 10b and 10c. Attached to the lens generally circular periphery are two oppositely extending, solid haptics 11 and 12. Loop type haptics may alternatively be employed. See the publication entitled "Simultaneously Endocapsular Implantation of Haptics and Optic Segment Using Cross-Action Folding Forceps", by Henry H. McDonald, M.D.

In accordance with one aspect of the invention, the lens also has two opposed peripheral segments 13 and 14 which are characterized as light blocking. They may be internally darkened, or cloudy, or occluded, or the surfaces of the segments may be treated so as to be irregular, or occluded or darkened, to achieve light blocking effect. See light rays 15 in FIG. 2, blocked by 13 and 14, whereas light rays 16 incident on the lens light passing and refracting intermediate portion 10a are not blocked, and pass from the lens at 16a. Further, the segments 13 and 14 have substantially reduced thickness (de-bulking) over their major extents, relative to the thickness of 10a over its major extent. Note also that the two segments typically have substantially equal size and shape, and they extend adjacent the intermediate optics portion 10a along substantially linear and parallel borders 20 and 21 as seen in FIG. 1. Such borders appear as planes 20' and 21' in FIG. 2. Also, the segments have generally convex outer edges 13a and 14a. Typical dimensions are as follows:

$$d \simeq 6 \text{ mm}$$
$$e \simeq 3 \text{ to } 4 \text{ mm}$$

where "d" is the diameter of the intermediate portion 10a, and "e" is the spacing between the segments, as seen in FIG. 1.

As also seen in FIG. 1, the lens has an optical axis 23, and there is a flat plane 24 containing that axis 23 that bisects both of the segments. That plane extends generally normal to the parallel, linear borders 20 and 21. Plane 24 also bisects the lens intermediate portion 10a. Each of the segments 13 and 14 has thickness which tapers or reduces, directionally away from the intermediate portion 10a, as is seen in FIG. 2. Thus, the segments are de-bulked relative to intermediate portion 10a.

The haptics 11 and 12 are in the form of flat, foldable and flexible plastic tabs that extend directionally longitudinally oppositely—see arrows 25 and 26 in FIG. 1, whereby each segment 13 and 14 is elongated in skewed relation to the longitudinal direction of tab elongation. As will appear, these relationships facilitate superposition of the reduced thickness segments 13 and 14 during lens and tab folding, to minimize the overall width of the folded assembly for insertion through an incision in the corneo-scleral limbus. Also, as is clear from FIG. 2, the haptics have secure attachment to the lens at lens peripheral regions 70 and 71, offset from the thin segments 13 and 14 which offer less secure attachment of the haptics to the lens.

The lens also defines a fold axis 30 that bisects the intermediate optical portion 10a. See FIGS. 1, 3, 4, 5 and 6, the axis 30 passing through axis 23. Segments 13 and 14 are elongated in generally parallel relation to that fold axis 30, which extends crosswise of the longitudinal axis 34 of haptic elongation, at an acute angle $\alpha$, as seen in FIG. 3. Axis 34 also passes through axis 23.

FIGS. 5 and 6 show the resiliently foldable lens as having been folded along axis 30 to bring the de-bulked two segments 13 and 14 into superposition, i.e. maintains the segments in parallel, closely spaced relation. De-bulking of the lens segments 13 and 14 accordingly allows for forceps gripping of the lens at pockets formed by the outwardly facing tapered surfaces 13b and 14b of the segments, as seen in FIG. 10, significantly enhancing grippability of the folded lens by the forceps, and resultant assurance against forceps displacement relative to the lens as during folding, maneuvered insertion of the lens and haptics through a narrow width wound (for example about 3 mm) in the eye, as referred to, rotation of the folded lens in the eye to position the haptics, and during lens release to control said release and prevent lens "explosive" unfolding. See the forceps blades 40 and 41 in FIG. 10, received in the pockets shown.

Cross-over type forceps may be employed for lens insertion into the eye "bag", as described in U.S. Pat. No. 4,813,957. FIGS. 11 and 12 show another type forceps 42 holding a lens 10, FIG. 12 showing the forceps controllably expanded to release the lens. FIG. 7 shows the use of cross-over forceps 44 (see cross-over point 45), with blades 40 and 41 extending in parallel relation, and placed adjacent segments 13 and 14. Blade an of a holding forceps 46 projects oppositely as shown, as along the fold axis 30, to hold or position the lens 10 during folding. The forceps blades 40 and 41 may be pressed downwardly to fold the lens about axis 30. See FIG. 9, steps (c) through (g), showing progressive lens folding as blades 40 and 41 are pressed down relative to blade 46. Blades 40 and 41 remain in the pockets formed by segment surfaces 13b and 14b (see FIG. 10) during such folding, the blades also being closed partially together during lens folding. Blade 46a is axially withdrawn as at or near step 9(f). FIG. 9(a) shows a wound or incision 50 in the eye, and FIG. 9(b) shows a lens 10a, of FIGS. 1 and 2 type, haptics not being shown.

FIGS. 13 and 14 show insertion of the folded lens and haptics into an eye lens zone, via the narrow wound, and via the opening 50 of the anterior capsulatory 50. In FIG. 14 the folded lens and haptics are inserted more deeply than in FIG. 13, and the corner 11e of the forward haptic 11, becomes folded back, as shown.

FIG. 15 shows the unfolded lens and haptics in the eye 60. Segments 13 and 14 are positioned (by lens rotation) to extend generally horizontally, above and below the lens intermediate portion 10a; i.e. the portion 10a is elongated left and right to pass maximum left and right light through the lens to the eye retina, i.e. the effective width of the lens is not reduced, so as not to inhibit left and right vision. The occluded de-bulked segments 13 and 14 block light passage (light that would otherwise be distorted due to thinning or de-bulking at 13 and 14); but any inhibition of up-down vision is of lesser importance and such up-down vision is normally inhibited anyway by squinting of eyelids. The normal pupil appears at 61, and the expanded pupil at 61a.

Looping haptics may be employed in place of the tab-like haptics described.

In FIG. 10, not that the total thickness of the superposed two blades and two segments is substantially the same or less than the total thickness of the two halves of the folded intermediate optical portion of the lens.

I claim:

1. A foldable plastic lens insertable into the eye lens zone from which a natural lens has been removed, comprising
    a) the plastic lens having a light passing intermediate optical portion, and two oppositely extending haptics,
    b) the lens also having two opposed peripheral segments characterized as light blocking,
    c) said segments having substantially reduced thickness relative to the thickness or thicknesses of said intermediate optical portion,
    d) said haptics being in the form of flat, foldable plastic elements that extend directionally longitudinally oppositely, said segments each elongated in skewed relation to said longitudinal direction.

2. The lens of claim 1 wherein said two segments are of substantially equal size and shape.

3. The lens of claim 1 wherein each of said segments extends adjacent said intermediate optical portion along a substantially linear border.

4. The lens of claim 1 wherein the lens has an optical axis, and there being a flat plane containing said optical axis which bisects one of said segments and also bisects the other of said segments.

5. The lens of claim 4 wherein said plane also bisects said intermediate optical portion of the lens.

6. The lens of claim 1 wherein said lens defines a fold axis that bisects said intermediate optical portion, said segments elongated in generally parallel relation with said fold axis.

7. The lens of claim 6 wherein said fold axis extends crosswise of said longitudinal axis and is angled relative thereto.

8. The lens of claim 6 wherein the lens is folded at said fold axis to bring said segments into superposition for insertion through an eye incision into the eye corneo-scleral limbus.

9. The lens of claim 1 wherein each of said segments has thickness which is tapered away from said intermediate optical portion of the lens.

10. A foldable silicon plastic lens insertable into the eye lens zone from which a natural lens has been removed, that comprises
    a) the lens having a light passing main optical portion and having at least one peripheral segment characterized as light blocking, the lens having haptics that extend directionally longitudinally oppositely,
    b) said at least one segment having substantially reduced thickness over its major areal extent relative to the thickness or thicknesses of said main optical portion,
    c) said at least one segment being elongated in skewed relation to said longitudinal direction.

11. The lens of claim 10 including flexible haptic means connected to the periphery of said lens.

12. The lens of claim 11 wherein said haptic means is connected to the periphery of said main optical portion and also to the periphery of said segment.

13. A cross-over forceps in combination with a foldable plastic lens insertable into the eye lens zone from which a natural lens has been removed, comprising
    a) the plastic lens having a light passing intermediate optical portion, and two oppositely extending haptics,
    b) the lens also having two opposed peripheral segments characterized as light blocking,
    c) said segments having substantially reduced thickness relative to the thickness of said intermediate optical portion,
    d) said haptics being in the form of flat, foldable plastic elements that extend directionally longitudinally oppositely, said segments each elongated in skewed relation to said longitudinal direction,
    e) said lens defining a fold axis that bisects said intermediate optical portion, said segments elongated in generally parallel relation with said fold axis,
    f) said fold axis extending crosswise of said longitudinal axis and being angled relative thereto,
    g) the lens being folded at said fold axis to bring said segments into superposition for insertion through an eye incision into the eye corneo-scleral limbus,
    h) and wherein said cross-over forceps has two blades which grip the folded lens at one side of each of said reduced thickness segments, whereby the total thickness of the superposed two blades and two segments is substantially the same or less than the total thickness of the two halves of the folded intermediate optical portion of the lens.

* * * * *